United States Patent
Horn

(10) Patent No.: US 10,010,610 B2
(45) Date of Patent: Jul. 3, 2018

(54) COMPOSITIONS AND METHODS FOR THE TREATMENT OF INTRAOCULAR NEOVASCULARIZATION AND/OR LEAKAGE

(71) Applicant: Retinal Therapies LLC, Coronado, CA (US)

(72) Inventor: Gerald Horn, Deerfield, IL (US)

(73) Assignee: Retinal Therapies, LLC, Coronado, CA (US)

( * ) Notice: Subject to any disclaimer, the term of this patent is extended or adjusted under 35 U.S.C. 154(b) by 0 days.

(21) Appl. No.: 14/593,704

(22) Filed: Jan. 9, 2015

(65) Prior Publication Data
US 2015/0196649 A1    Jul. 16, 2015

Related U.S. Application Data

(60) Provisional application No. 61/969,861, filed on Mar. 25, 2014, provisional application No. 61/928,061, filed on Jan. 16, 2014.

(51) Int. Cl.
| | |
|---|---|
| A61K 47/10 | (2017.01) |
| A61K 47/20 | (2006.01) |
| A61K 47/22 | (2006.01) |
| A61K 47/38 | (2006.01) |
| A61K 31/47 | (2006.01) |
| A61K 31/437 | (2006.01) |
| A61K 31/4439 | (2006.01) |
| A61K 31/4709 | (2006.01) |
| A61K 31/53 | (2006.01) |
| A61K 9/00 | (2006.01) |
| A61K 47/26 | (2006.01) |
| A61K 9/107 | (2006.01) |

(52) U.S. Cl.
CPC ............ *A61K 47/20* (2013.01); *A61K 9/0048* (2013.01); *A61K 9/107* (2013.01); *A61K 31/437* (2013.01); *A61K 31/4439* (2013.01); *A61K 31/47* (2013.01); *A61K 31/4709* (2013.01); *A61K 31/53* (2013.01); *A61K 47/10* (2013.01); *A61K 47/26* (2013.01)

(58) Field of Classification Search
CPC ........ A61K 47/10; A61K 47/20; A61K 47/22; A61K 31/47
See application file for complete search history.

(56) References Cited

U.S. PATENT DOCUMENTS

| | | | |
|---|---|---|---|
| 6,482,799 B1 * | 11/2002 | Tuse ..................... | A61L 12/14 422/28 |
| 8,465,778 B2 | 6/2013 | Hughes et al. | |
| 8,481,069 B2 | 7/2013 | Hughes et al. | |
| 2014/0206764 A1 * | 7/2014 | Liu ...................... | A61K 9/0048 514/560 |
| 2015/0164906 A1 * | 6/2015 | Zack .................... | A61K 45/06 514/235.2 |

OTHER PUBLICATIONS

Berge, SM, Pharmaceutical Salts, J Pharm Sci, Jan. 1977, 66(1), 1-19.
Kratz, F, Albumin as a drug carrier: design of prodrugs, drug conjugates and nanoparticles, J Control Release, Dec. 18, 2008, 132(3), 171-83, Epub May 17, 2008.
Elsadek, B, et al., Impact of albumin on drug delivery—new applications on the horizon, J Control Release, Jan. 10, 2012, 157(1), 4-28, Epub Sep. 16, 2011.
Ajaj, KA, et al., In vitro and in vivo study of an albumin-binding prodrug of doxorubicin that is cleaved by cathepsin B, Cancer Chemother Pharmacol, Jul. 2009, 64(2), 413-8, Epub Feb. 20, 2009.
Chawla, SP, et al., A phase 1B/2 study of aldoxorubicin in patients with soft tissue sarcoma, Cancer, Feb. 15, 2015, 121(4), 570-9, Epub Oct. 13, 2014.
Sebag, J ed., Vitreous: in Health and Disease, 2014, Springer-Verlag New York, p. 3-12, Vitreous Proteins, Paul N Bishop.
Yang, C, et al., Intravitreal administration of dexamethasone-loaded PLGA-TPGS nanoparticles for the treatment of posterior segment diseases, J Biomed Nanotechnol, Sep. 2013, 9(9), 1617-23.
Banerjee, SS, et al., Poly(ethylene glycol)-Prodrug Conjugates: Concept, Design, and Applications, J Drug Deliv, 2012, 2012:103973, Epub May 7, 2012.
Lallemand, F, et al., Successfully improving ocular drug delivery using the cationic nanoemulsion, novasorb, J Drug Deliv, 2012, 2012:604204, Epub Feb. 27, 2012.
Su, J, et al., Synthesis, conjugation and evaluation of some novel polymers and their micro particles for sustained release drug formulations, Pak J Pharm Sci, Jul. 2013, 26(4):741-6, Abstract.
Zheng, YR, et al., Pt(IV) prodrugs designed to bind non-covalently to human serum albumin for drug delivery, J Am Chem Soc, Jun. 18, 2014, 136(24), 8790-8, Epub Jun. 6, 2014, Abstract.
Ciulla et al., Diabetic retinopathy and diabetic macular edema, Diabetes Care, 26(9), Sep. 2003, 2653-2664.

\* cited by examiner

*Primary Examiner* — Zohreh A Fay
(74) *Attorney, Agent, or Firm* — Wood, Phillips, Katz, Clark & Mortimer

(57) ABSTRACT

The invention provides compositions and methods for the treatment of intraocular neovascularization and/or leakage including wet age-related macular degeneration. The compositions preferably use tyrosine kinase inhibitors with an IC50 for VEGFR2 of 20 nanomolars or less and an IC50 for c-MET of 20 nanomolars or less.

8 Claims, No Drawings

COMPOSITIONS AND METHODS FOR THE TREATMENT OF INTRAOCULAR NEOVASCULARIZATION AND/OR LEAKAGE

BACKGROUND OF THE INVENTION

Macular degeneration is a disease of the eye that results in minor to severe impairment of the subject's sharp central vision, which is necessary for activities such as reading and driving. Age-related macular degeneration ("AMD") afflicts an estimated 30 to 50 million people worldwide and is the leading cause of severe vision loss in Western societies. Normal vision occurs when light enters the front of the eye and is focused by the lens onto highly sensitive and fragile cells called photoreceptors that line the inside of the back of the eye. Together with other neurons the photoreceptors make up the retina of the eye. The macula is the portion of the retina located near the center of the back of the eye that contains the fovea, which is responsible for sharp central vision. Like all cells, the photoreceptors need a constant supply of oxygen and nutrients; however, due to the sensitive nature of the structure of the retina it is not vascularized. Instead, the retina is fed by the choroid, a highly vascular layer outside the retina. The oxygen and nutrients from these blood vessels are transported to the retina across Bruch's membrane which consists of a layer of pigmented epithelium and layers of connective tissue.

AMD disrupts the photoreceptors of the macula in one of two ways: (1) deposits of extracellular debris between Bruch's membrane and the retinal pigment epithelium known as "dry" macular degeneration and (2) breaks in Bruch's membrane that allow angiogenic blood vessels from the choroid to penetrate the retinal pigment epithelium known as "wet" macular degeneration. Dry AMD progresses slowly and is responsible for about 90% of AMD worldwide. Wet AMD can be sudden, severe and irreversible due to bleeding and scarring of the macular region including the fovea. Although wet AMD accounts for only 10% of AMD worldwide it is responsible for 90% of AMD-associated blindness.

The intraocular neovascularization that occurs in wet AMD is confined to the macula but it may also occur at other places in the uveal tract including the adjacent posterior pole and even more anteriorly at the trabecular meshwork of the iris root. Such neovascularization can occur from a variety of pathologies other than AMD including but not limited to proliferative disorders, infectious disorders, genetic disorders, vascular diseases, exudative diseases, uveitis, retinitis, choroiditis, trauma including surgery and other causes of ischemia or angiogenesis.

Vascular endothelial growth factor receptor ("VEGFR") pathways are the main pharmaceutical targets of angiogenic suppression. Anti-angiogenesis drugs that target VEGFR pathways and are used in the eye include pegaptanib (Macugen®; Macugen is a registered trademark of Eyetech, Inc.), bevacizumab (Avastin®; Avastin is a registered trademark of Genentech, Inc.) and ranibizumab (Lucentis®; Lucentis is a registered trademark of Genentech, Inc.). However, each of these drugs is administered in the form of an injection due to their relatively large size and poor absorption. Additionally, these drugs are expensive to administer. For example, ranibizumab can cost up to $48,000 for the two-years of recommended treatment. Perhaps more prohibitive than the cost is the side effects of these intraocularly injected drugs including redness or petechial hemorrhage in the white part of the eye, eye pain lasting for several hours, cataracts, vitreous floaters (i.e. specks in your vision), increase pressure within the eye, inflammation of the eye, blurred vision, eye irritation, and most prohibitive, risk of endophthalmitis.

Additional tyrosine kinase receptors ("ancillary receptors") involved in angiogenesis have also been discovered. The suppression of these ancillary receptors is known to enhance the anti-angiogenic effect of VEGFR pathway suppression. These ancillary receptors include platelet-derived growth factor receptors ("PDGFR") α and β, fibroblast-derived growth factor receptors ("FDGFR") 1-4, c-KIT, and TIE 1-3. Suppression of two or more of these ancillary receptors in conjunction with suppression of a VEGFR is common in the art and is known as multi-receptor tyrosine kinase inhibition. Multi-receptor tyrosine kinase inhibition for treatment of angiogenesis is known to decrease the incidence and severity of tachyphylaxis or resistance in response to suppression of a VEGFR alone. Pharmaceuticals used in multi-receptor tyrosine kinase inhibition generally have high degrees of lipophilicity with insufficient penetration to the posterior pole of the eye and those with sufficient penetration have an insufficient duration of activity. Many of the molecules used in multi-receptor tyrosine kinase inhibition have a risk of severe systemic side effects due to their chemotherapeutic side effects with high systemic absorption. Attempts to overcome these insufficiencies and side effect include slow release intra-vitreal implants as described in U.S. Pat. Nos. 8,481,069 and 8,465,778. However, intra-vitreal implants have their own disadvantages including pain, transient blurring of vision for tens of minutes to hours, major risks and expense of an intraocular surgical procedure including need for possible implant removal, greater risk of fulminant endophthalmitis, acute or indolent inflammation with cystoids macular edema, vitritis, cyclitis, retinal detachment, choroidal effusion and toxicity form dissolution of the implant membranes.

Thus, there is a need in the art for an ophthalmological composition and methods that can deliver sufficient amounts of these poorly absorbed and difficult to solubilize drugs intraocularly to the posterior of the eye where wet AMD and several other angiogenic disease processes occur. These compositions should be cheap to produce and these methods should be easy to perform, such as with topological compositions or subconjunctival injections, thus avoiding the expense, inconvenience and morbidity of repeated intra-vitreal injections. Furthermore, these compositions and methods should avoid expensive and invasive surgical procedures, such as the intra-vitreal implant. Additionally, these ophthalmological compositions and methods should be able to achieve topological delivery to the posterior of the eye without high systemic absorption of anti-angiogenic drugs that often lead to system toxicities including severe bleeding, disturbed wound healing, gastro-intestinal perforation, hypertension, fatigue, and on rare occasions, death. Finally, these ophthalmological compositions and methods should have improved efficacy over commercially available treatments for wet AMD and other diseases caused by intraocular neovascularization via reduction or elimination of resistance and tachyphylaxis.

SUMMARY OF THE INVENTION

In one embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In one embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 10 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 5 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 2 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 2 nanomolar or less, wherein the IC50 for c-MET is about 2 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 20 nanomolar or less, wherein the route of administration is topical, subconjunctival injection or a combination thereof and wherein the lipophilicity of each of the one or more tyrosine kinase inhibitors is from about Log P 1.0 to about Log P 5.0.

In another embodiment, the present invention provides an ophthalmological composition comprising one or more tyrosine kinase inhibitors or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 20 nanomolar or less, wherein the route of administration is topical, subconjunctival injection or a combination thereof and wherein the lipophilicity of each of the one or more tyrosine kinase inhibitors is from about Log P 2.5 to about Log P 3.5.

In another embodiment, the present invention provides an ophthalmological composition comprising one or more tyrosine kinase inhibitors or any pharmaceutically acceptable salts, esters, or prodrugs thereof and a surfactant, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof and a surfactant, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof and polyoxyl 35 or 40 castor oil or polyoxyl 35 or 40 stearate and or a cyclodextrin (e.g. a negatively charged gamma cyclodextrin such as Captisol®) or combination thereof, at a concentration from about 1% to about 15% weight by volume, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, polyoxyl 40 castor oil or polyoxyl 40 stearate at a concentration from about 1% to about 15% weight by volume and a viscosity enhancer selected from the group consisting of carboxymethyl cellulose, carboxypropylmethyl cellulose, hydroxypropyl cellulose, hydroxyethyl cellulose, and hydroxypropylmethyl cellulose or a combination thereof, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, polyoxyl 40 castor oil or polyoxyl 40 stearate at a concentration from about 1% to about 15% weight by volume and a viscosity enhancer selected from the group consisting of carboxymethyl cellulose, carboxypropylmethyl cellulose, hydroxypropyl cellulose, hydroxyethyl cellulose, and hydroxypropylmethyl cellulose or a combination thereof, wherein the half maximal inhibitory concentration (IC50) for vascular endothelial growth factor receptor 2 (VEGFR2) is about 20 nanomolar or less, wherein the IC50 for c-MET is about 20 nanomolar or less, wherein the route of administration is topical, subconjunctival injection or a combination thereof and wherein the final composition has a viscosity between 50 and 100 cps between blinks; a viscosity between 5 and 25 cps during a blink; and the ratio of viscosity upon instillation to viscosity during or after a blink is about 3 to 1 or greater.

In another embodiment, the present invention provides an ophthalmological composition comprising one or more tyrosine kinase inhibitors or any pharmaceutically acceptable salts, esters, or prodrugs thereof and propanediol at a concentration from about 1% to about 10% weight by volume, wherein the half maximal inhibitory concentration (IC50)

for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, propanediol at a concentration from about 1% to about 10% weight by volume and one or more surfactants or lipid solubilizers each at a concentration from about 1% to about 21% weight by volume, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof and one or more surfactants or lipid solubilizers selected from the group consisting of sodium lauryl ether sulfate, sodium lauryl sulfate, dimethyl isosorbide, Span® 20-80, a cyclodextrin (e.g. Captisol®), squalene, a second propylene glycol, a polyethylene glycol (preferably a low molecular weight such as PEG 400), a polysorbate, a poloxamer, a polyoxyl and a combination thereof, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, sodium lauryl sulfate at a concentration from about 0.5% to about 10.0% weight by volume and propanediol at a concentration of about 1% to 10% weight by volume, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, sodium lauryl sulfate at a concentration from about 0.5% to about 10.0% weight by volume and propanediol at a concentration of about 1% to 10% weight by volume and a viscosity enhancer selected from the group consisting of carboxymethyl cellulose, carboxypropylmethyl cellulose, hydroxypropyl cellulose, hydroxyethyl cellulose, and hydroxypropylmethyl cellulose or a combination thereof, wherein the half maximal inhibitory concentration (IC50) for vascular endothelial growth factor receptor 2 (VEGFR2) is about 20 nanomolar or less, wherein the IC50 for c-MET is about 20 nanomolar or less and wherein the route of administration is topical, subconjunctival injection or a combination thereof.

In another embodiment, the present invention provides an ophthalmological composition comprising one or more tyrosine kinase inhibitors or any pharmaceutically acceptable salts, esters, or prodrugs thereof, sodium lauryl sulfate at a concentration from about 0.5% to about 10.0% weight by volume and propanediol at a concentration of about 1% to 10% weight by volume and a viscosity enhancer selected from the group consisting of carboxymethyl cellulose, carboxypropylmethyl cellulose, hydroxypropyl cellulose, hydroxyethyl cellulose, and hydroxypropylmethyl cellulose or a combination thereof, wherein the half maximal inhibitory concentration (IC50) for vascular endothelial growth factor receptor 2 (VEGFR2) is about 20 nanomolar or less, wherein the IC50 for c-MET is about 20 nanomolar or less, wherein the route of administration is topical, subconjunctival injection or a combination thereof and wherein the final composition has a viscosity between 50 and 100 cps between blinks; a viscosity between 5 and 25 cps during a blink; and the ratio of viscosity upon instillation to viscosity during or after a blink is about 3 to 1 or greater.

In a preferred embodiment, the present invention provides an ophthalmological composition comprising one tyrosine kinase inhibitor selected from the group consisting of cabozantinib, pazopanib, foretinib, and MGCD-265 or any pharmaceutically acceptable salts, esters, or prodrugs thereof, wherein the half maximal inhibitory concentration (IC50) for vascular endothelial growth factor receptor 2 (VEGFR2) is about 20 nanomolar or less, wherein the IC50 for c-MET is about 10 nanomolar or less and wherein the route of administration is topical, subconjunctival injection or a combination thereof.

In another embodiment, the present invention provides an ophthalmological composition comprising two tyrosine kinase inhibitors consisting of a first tyrosine kinase inhibitor and a second tyrosine kinase inhibitor, wherein the first tyrosine kinase inhibitor has an IC50 for VEGFR of about 20 nanomolar or less, wherein the second tyrosine kinase inhibitor has an IC50 for c-MET of about 10 nanomolar or less and wherein the route of administration is topical, subconjunctival injection or a combination thereof.

In another embodiment, the present invention provides an ophthalmological composition comprising two tyrosine kinase inhibitors consisting of a first tyrosine kinase inhibitor and a second tyrosine kinase inhibitor, wherein a first tyrosine kinase inhibitor is selected from the group consisting of axitinib, cabozantinib, foretinib, regorafenib, ponatinib, motesanib, cediranib, tivozanib, sorafenib, LY2457546 and MGCD-265 and wherein a second tyrosine kinase inhibitor is selected from the group consisting of cabozantinib, tivantinib, AMG458, JNJ-3887, EMD1214063, BMS794833, PHI1665752, SGX-523 and INCB280 and wherein the route of administration is topical, subconjunctival injection or a combination thereof.

In another embodiment, the present invention provides an ophthalmological composition comprising two tyrosine kinase inhibitors consisting of a first tyrosine kinase inhibitor selected from axitinib or tivozanib and a second tyrosine kinase inhibitor selected from INCB280 or tivantinib and wherein the route of administration is topical, subconjunctival injection or a combination thereof.

In one embodiment, the present invention provides a method for treating a disease caused by intraocular neovascularization comprising administering to a patient in need thereof a composition of the present invention.

In another embodiment, the present invention provides a method for treating dry macular degeneration, wet age-related macular degeneration, diabetic macular edema, diabetic proliferative retinopathy, or diabetic vitreoretinal traction comprising administering to a patient in need thereof a composition of the present invention.

In one embodiment, the present invention provides a method of storing a lyophilized tyrosine kinase inhibitor separately from an ophthalmologically effective diluent prior to instillation in an eye of a patient in need thereof comprising the steps of:

placing the lyophilized tyrosine kinase inhibitor in a first chamber of a two-chambered unit dose container consisting of an impermeable thin membrane separating the first chamber base and a second chamber;

sealing the first chamber;

placing the diluent in the second chamber;

sealing the second chamber;

wherein rupturing of the impermeable thin membrane creates a solution or a suspension of the lyophilized tyrosine kinase inhibitor prior to installation in the eye of the patient.

In another embodiment, the present invention provides a method of storing a lyophilized tyrosine kinase inhibitor separately from an ophthalmologically effective diluent prior to instillation in an eye of a patient in need thereof comprising the steps of:

placing the lyophilized tyrosine kinase inhibitor in a first chamber of a two-chambered unit dose container consisting of an impermeable thin membrane separating the first chamber base and a second chamber;

sealing the first chamber;

placing the diluent in the second chamber;

sealing the second chamber;

wherein rupturing of the impermeable thin membrane creates a solution or a suspension of the lyophilized tyrosine kinase inhibitor prior to installation in the eye of the patient and wherein the sealing of the first chamber consists of vacuum sealing, purging the first chamber with nitrogen or a combination thereof.

DETAILED DESCRIPTION OF THE INVENTION

Definitions

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, or slowing the progress of the disease, disorder, or condition to which such terms apply, or one or more symptoms of such disease, disorder, or condition.

Unless stated otherwise, all percentages for ingredients are weight per volume (w/v) and % w/v refers to the percent weight of the final composition unless stated otherwise.

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

The term "pharmaceutically acceptable" describes a material that is not biologically or otherwise undesirable, i.e., without causing an unacceptable level of undesirable biological effects or interacting in a deleterious manner.

As used herein, the term "effective amount" refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful subject benefit. Thus, an "effective amount" will depend upon the context in which it is being administered. An effective amount may be administered in one or more prophylactic or therapeutic administrations.

The term "prodrugs" refers to compounds, including monomers and dimers of the compounds of the invention, which have cleavable groups and become under physiological conditions compounds which are pharmaceutically active in vivo.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

The compounds of the present invention can be used in the form of pharmaceutically acceptable salts derived from inorganic or organic acids or bases. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq.

The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, malic acid, sulphuric acid and phosphoric acid and such organic acids as oxalic acid, malic acid, maleic acid, methanosulfonic acid, succinic acid and citric acid. Preferred acid addition salts are prepared from methanosulfonic acid, malic acid and phosphoric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, a heteroaryl group or other suitable substituent.

As used herein the term "patient" refers but is not limited to a person or other animal.

As used herein the term "dropwise" refers to any method of incrementally adding one solution to another solution.

Compounds

Tyrosine kinase inhibitors ("TKI") preferred for the present invention include those TKI's that have a half maximal inhibitory concentration (IC50) for vascular endothelial growth factor receptor 2 ("VEGFR2") of about 20 nanomolar or less and an IC50 for c-MET of about 10 nanomolar or less, which include, but are not limited to, cabozantinib, pazopanib, foretinib, MGCD-265 and [Kala pharma compound] or any pharmaceutically acceptable salts, esters, or prodrugs thereof. In a more preferred embodiment the TKI is cabozantinib or foretinib. Alternatively, TKI's preferred for the present invention include those TKI's that have a half maximal inhibitory concentration (IC50) for vascular endothelial growth factor receptor 2 ("VEGFR2") of about 20 nanomolar or less, which include, but are not limited to, axitinib, cabozantinib, foretinib, regorafenib, ponatinib, motesanib, cediranib, tivozanib, sorafenib, LY2457546, and MGCD-265 or any pharmaceutically acceptable salts, esters, or prodrugs thereof combined with TKIs that have an IC50 for c-MET of about 10 nanomolar or less, which include, but are not limited to cabozantinib, tivantinib, AMG458, JNJ-3887, EMD1214063, BMS794833, PHI1665752, SGX-523 and INCB280 or any pharmaceutically acceptable salts, esters, or prodrugs thereof. In a more preferred embodiment the TKI's are axitinib or tivozanib combined with INCB280. Additionally, preferred TKI's of the present invention have a Log P value (octanol-water partition coefficient at pH 7.0) from about 1.0 to about 5.0 More preferably the Log P value is from about 2.5 to about 3.5.

For example, a preferred TKI of the present invention, cabozantinib has an IC50 for VEGFR2 of 0.035 nanomolar, an IC50 for c-MET of 1.3 nanomolar and a Log P of 3.0.

The c-MET receptor (a.k.a. hepatocyte growth factor receptor) is associated with tumor aggressiveness, particularly in hypoxic conditions post anti-angiogenic therapy where neovascularization is suppressed. Surprisingly, inhibition of the c-MET receptor is discovered to provide the only necessary ancillary receptor inhibition for powerful anti-angiogenic suppression Inhibition of VEGFR2 and c-MET produced from minimal to absent resistance and tachyphylaxis.

Surfactants suitable for the present invention include, but are not limited to, nonionic, cationic and/or anionic surfactants. Specific surfactants include cyclodextrins, polyoxyl alkyls, poloxamers or combinations thereof. Preferred embodiments include polyoxyl 35 castor oil or polyoxyl 40 stearate. Further, substitution of other surfactants compatible with ophthalmic use allows for similar formulation advantages, which may included but is not limited to one or more of a nonionizing surfactant such as poloxamer, Poloxamer 188, Poloxamer 407, Polysorbate 20, Polysorbate 80, ionically charged (e.g. anionic) beta-cyclodextrins with or without a butyrated salt (Captisol®; Captisol is a registered trademark of Cydex Pharmaceuticals), 2-hydroxypropyl beta cyclodextrin ("HPβCD"), Polyoxyl 35 stearate, Polyoxyl 40 castor oil and Polyoxyl 40 hydrogenated castor oil, poloxamer 103, poloxamer 123, and poloxamer 124, poloxamer 407, poloxamer 188, and poloxamer 338, any poloxamer analogue or derivative, polysorbate, polysorbate 20, polysorbate 40, polysorbate 60, polysorbate 80, any polysorbate analogue or derivative, cyclodextrin, hydroxypropyl-β-cyclodextrin, hydroxypropyl-γ-cyclodextrin, randomly methylated β-cyclodextrin, β-cyclodextrin sulfobutyl ether, γ-cyclodextrin sulfobutyl ether or glucosyl-β-cyclodextrin, any cyclodextrin analogue or derivative, polyoxyethylene, polyoxypropylene glycol, an polysorbate analogue or derivative, polyoxyethylene hydrogenated castor oil 60, polyoxyethylene (200), polyoxypropylene glycol (70), polyoxyethylene hydrogenated castor oil, polyoxyethylene hydrogenated castor oil 60, polyoxol, polyoxyl stearate, nonoxynol, octyphenol ethoxylates, nonyl phenol ethoxylates, capryols, lauroglycol, PEG, Brij 35, glyceryl laurate, lauryl glucoside, decyl glucoside, or cetyl alcohol; or zwitterion surfactants such as palmitoyl carnitine, cocamide DEA, cocamide DEA derivatives cocamidopropyl betaine, or trimethyl glycine betaine, N-2(2-acetamido)-2-aminoethane sulfonic acid (ACES), N-2-acetamido iminodiacetic acid (ADA), N,N-bis(2-hydroxyethyl)-2-aminoethane sulfonic acid (BES), 2-[Bis-(2-hydroxyethyl)-amino]-2-hydroxymethyl-propane-1,3-diol (Bis-Tris), 3-cyclohexylamino-1-propane sulfonic acid (CAPS), 2-cyclohexylamino-1-ethane sulfonic acid (CHES), N,N-bis(2-hydroxyethyl)-3-amino-2-hydroxypropane sulfonic acid (DIPSO), 4-(2-hydroxyethyl)-1-piperazine propane sulfonic acid (EPPS), N-2-hydroxyethylpiperazine-N'-2-ethane sulfonic acid (HEPES), 2-(N-morpholino)-ethane sulfonic acid (MES), 4-(N-morpholino)-butane sulfonic acid (MOBS), 2-(N-morpholino)-propane sulfonic acid (MOPS), 3-morpholino-2-hydroxypropanesulfonic acid (MOPSO), 1,4-piperazine-bis-(ethane sulfonic acid) (PIPES), piperazine-N,N'-bis(2-hydroxypropane sulfonic acid) (POPSO), N-tris(hydroxymethyl)methyl-2-aminopropane sulfonic acid (TAPS), N-[tris(hydroxymethyl)methyl]-3-amino-2-hydroxypropane sulfonic acid (TAPSO), N-tris(hydroxymethyl) methyl-2-aminoethane sulfonic acid (TES), 2-Amino-2-hydroxymethyl-propane-1,3-diol (Tris), tyloxapol Span® 20-80 (sorbitan monolaurate, sorbitan monopalmitate, sorbitan monostearate, and sorbitan monooleate; Span is a registered trademark of Uniqema Americas Inc.) and Tween® 20-80 (polysorbate 20-80, Tween is a registered trademark of Uniqema Americas Inc.).

In another preferred embodiment of the invention propanediol can be used in combination with a surfactant or a lipid solubilizer instead of polyoxyl 40 or 35 castor oil or polyoxyl 40 or 35 stearate alone. Lipid solubilizers suitable for the present invention include, but are not limited to, alcohols, polyols, amides, esters, propylene glycol ethers and mixtures thereof. The preferred lipid solubilizer is dimethyl isosorbide. When used in combination with propanediol the preferred surfactant and/or lipid solubilizer is a polysorbate, a poloxamer, a cyclodextrin, Span® 20-80, dimethyl isosorbide or a combination thereof. In a more preferred embodiment propanediol is used in combination with dimethyl isosorbide and Span 20®.

Viscosity enhancers suitable for the present invention include, but are not limited to, carboxymethyl cellulose ("CMC"), methylcellulose, methyl cellulose 4000, hydroxymethyl cellulose, hydroxypropyl cellulose, hydroxypropylmethyl cellulose, hydroxyl propyl methyl cellulose 2906, carboxypropylmethyl cellulose, hydroxyethyl cellulose, or hydroxyethyl cellulose, hyaluronic acid, dextran, polyethylene glycol, polyvinyl alcohol, polyvinyl pyrrolidone, gellan, carrageenan, alignic acid, carboxyvinyl polymer or combinations thereof. In a preferred embodiment the viscosity enhancer will have an equilibration viscosity between 10 centipoise ("cps") and 100 cps between eyelid blinks, preferably between 50 and 100 cps and 30 cps or less, preferably between 5 and 25 cps during an eyelid blink. In a preferred embodiment the viscosity enhancer is 0.62% CMC to 0.87% CMC, more preferably from 0.75% to 0.87% w/v CMC (1%=2,500 centipoise), and most preferably 0.80% w/v CMC (1%=2,500 centipoise).

Once applied topically an initial viscosity well above 20 cps reduces or prevents systemic absorption including nasolacrimal, turbinate and conjunctival and scleral absorption into the vasculature. A non-Newtonian equilibrium results in tens of seconds that for a preferred embodiment reduces the initial viscosity from about 70-100 cps or greater to less than 20 cps at high shear ($^1/_{1000}$) as occurs during a blink allowing outstanding vision, to about 40-90 cps at low shear (1/s) between blinks. The result is a 10 fold or greater increase in viscosity versus tears or aqueous solutions that further retards nasolacrimal absorption and nasolacrimal pump effects on lid blink. This retardation allows for outstanding residence time of the drug. This residence time is achieved without systemic side from nasolacrimal vascular entry into the circulation, suppressing direct effects of high systemic absorption of anti-angiogenic tyrosine kinase inhibitors including severe bleeding, disturbed wound healing, gastro-intestinal perforation, hypertension and fatigue. Even in situ gels, with their extreme viscosity of 500-20,000 cps or greater will fractionate on blinking, allowing some small breakdown particles to drain through the nasolacrimal duct and increase systemic toxicity unless supplemented with a viscosity enhancer. Proper viscosity response is essential to topical or subconjunctival administration of TKI's as TKI's used for treating angiogenesis induce side effects when introduced systematically into the vasculature that include but are not limited to:

A) Constitutional including fatigue, anorexia, weight loss and depression;

B) Cardiovascular including hypertension, decreased left ventricular ejection fraction, and congestive failure, C) Gastrointestinal including stomatitis, nausea, diarrhea, and gastrointestinal perforation;

D) Metabolic including hand-foot syndrome, rash, xerosis, skin and hair depigmentation, and yellowing of the skin;

E) Renal including proteinuria, increased creatinine, and decreased renal function; and F) Hematologic and Laboratory including neutropenia, lymphopenia, thrombocytopenia, anemia, and increased transamines and lipases.

A tonicity adjustor can be, without limitation, a salt such as sodium chloride ("NaCl"), potassium chloride, mannitol or glycerin, or another pharmaceutically or ophthalmically acceptable tonicity adjustor. In certain embodiments the tonicity adjustor is 0.3% w/v glycerin. In other embodiments the tonicity adjustor is 0.037% w/v NaCl.

Preservatives that can be used with the present invention include, but not limited to, benzalkonium chloride (BAK), chlorobutanol, thimerosal, phenylmercuric acetate, disodium ethylenediaminetetraacetic acid, phenylmercuric nitrate, perborate or benzyl alcohol. In a preferred embodiment the preservative is BAK at a concentration of about 0.001% to about 1.0% w/v, more preferably at a concentration of about 0.02% w/v.

Various buffers and means for adjusting pH can be used to prepare ophthalmological compositions of the invention. Such buffers include, but are not limited to, acetate buffers, citrate buffers, phosphate buffers and borate buffers. It is understood that acids or bases can be used to adjust the pH of the composition as needed, preferably of 1 to 10 mM concentration, and more preferably about 5 mM. In a preferred embodiment the pH is from about 4.0 to about 8.0, in a more preferred embodiment the pH is from about 7.0 to about 7.5.

A large number of small anti-angiogenic TKI's including those preferred in the present invention are poorly soluble or emulsifiable and have poor penetration to the posterior portion of the eye where a major portion of diseases caused by intraocular neovascularization and/or leakage occur including wet AMD. Ophthalmological compositions and methods of the present invention are capable of solubilizing or emulsifying such TKI's, especially the subclass of TKI's with an IC50 for vascular endothelial growth factor receptor 2 ("VEGFR2") of about 20 nanomolar or less and/or an IC50 for c-MET of about 10 nanomolar or less and a lipophilicity defined by a Log P value of 1.0 to 5.0. This solubilization and/or emulsification allows for topical or subconjunctival delivery (or a combination of both) that in combination with the viscosity enhancers of the present invention achieve a high posterior eye segment concentration and duration of residence such that a posterior vitreous concentration of the TKI(s) effective to treat disease caused by intraocular neovascularization and/or leakage can be achieved without causing high levels of systemic absorption.

Diseases to be Treated with Compositions and Methods of the Invention

Disease that may be treated by compositions and methods of the present invention include, but are not limited to:

A) Maculopathies/Retinal degenerations including non-exudative (dry) AMD, exudative (wet) AMD, choroidal neovascularization, diabetic retinopathy, acute macular neuroretinopathy, central serous chorioretinopathy, cystoids macular edema and macular edema;

B) Uveitis/Retinitis/Choroiditis including acute multifocal placoid pigment epitheliopathy, Behcet's disease, Bird-shot retinochoroidopathy, infectious (syphilis, lime, tuberculosis, toxoplasmosis), intermediate uveitis (pars planitis), multifocal choroiditis, multiple evanescent white dot syndrome, ocular sarcoidosis, posterior scleritis, serpiginous choroiditis, subretinal fibrosis, uveitis syndrome, and Vogt-Koyanagi-Harada syndrome;

C) Vascular diseases/Exudative diseases including Coat's disease, parafoveal telangiectasis, papillophlebitis, frosted branch angitis, sickle cell retinopathy, other hemoglobin-opathies, angioid streaks and familial exudative vitreoretin-opathy;

D) Traumatic/surgical diseases including sympathetic ophthalmia, uveitic retinal disease, retinal detachment, trauma from laser photocoagulation or photodynamic therapy, hypoperfusion during surgery, radiation retinotherapy and bone marrow transplant retinopathy;

E) Proliferative disorders including proliferative vitreal retinotherapy, epiretinal membranes, proliferative diabetic retinopathy and retinopathy of prematurity (retrolental fibroplastic);

F) Infectious disorders including ocular histoplasmosis, ocular toxocariasis, presumed ocular histoplasmosis syndrome, endophthalmitis, toxoplasmosis, retinal diseases associated with HIV infection, choroidal disease associated with HIV infection, uveitic disease associated with HIV infection, viral retinitis, acute retinal necrosis, progressive outer retinal necrosis, fungal retinal diseases, ocular syphilis, ocular tuberculosis, diffuse unilateral subacute neuroretinitis and myiasis;

G) Genetic disorders including systemic disorders with associated retinal dystrophies, congenital stationary night blindness, cone dystrophies, fundus flavimaculatus, Best's disease, Pattern dystrophy of the retinal pigmented epithelium, X-linked retinoschisis, Sorsby's fundus dystrophy, benign concentric maculopathy, Bietti's crystalline dystrophy, psuedoxanthoma elasticum and Osler Weber syndrome;

H) Retinal tears/holes including retinal detachment, macular hole and giant retinal tear;

I) Tumors including retinal disease associated with tumors, solid tumors, tumor metastasis, benign tumors (e.g. hemangiomas, neurofibromas, trachomas, pyogenic granulomas), congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma and intraocular lymphoid tumors;

J) Neovascular ischemia including neovascular glaucoma, anterior segment ischemia syndromes, corneal neovascularization including post corneal surgery such as post penetrating keratoplasty, herpetic keratitis and other ischemic or corneal inflammatory conditions; and K) Miscellaneous diseases including punctuate inner choroidopathy, acute posterior multifocal placoid pigment epitheliopathy, myopic retinal degeneration and acute retinal pigment epithelitis and other diseases caused by intraocular neovascularization and/or leakage.

Compositions of the Invention

Compositions and methods of the inventions encompass all isomeric forms of the described ophthalmic drugs (and particularly α-2 adrenergic receptor agonists), their racemic mixtures, enol forms, solvated and unsolvated forms, analogs, prodrugs, derivatives, including but not limited to esters and ethers, and pharmaceutically acceptable salts, including acid addition salts.

The compositions of the present invention are preferably formulated for a mammal, and more preferably, for a human. In one embodiment of the invention, the compositions are delivered as ophthalmic solutions into the eyes. The invention contemplates both topical and subconjunctival administration including subconjunctival injection. They may also include additional non-therapeutic components, which include, but are not limited to, preservatives, delivery vehicles, tonicity adjustors, buffers, pH adjustors, antioxidants, tenacity adjusting agents, mucoadhesive agents, viscosity adjusting agents, and water.

The compositions of the present invention may comprise corneal permeation enhancing agents which include, but are not limited to, preservatives, cyclodextrins, viscosity enhancers, and ion-channel enhancing agents. In some embodiments, corneal permeation enhancing agents include citrate, a citrate salt and/or other salts which increase solubility, chelating agents such as disodium ethylenediaminetetraacetic acid ("EDTA"), preservatives, ion-channeling agents, cyclodextrin, or other additives which increase corneal permeability.

In some embodiments of the invention, a corneal permeation enhancing agent may be selected from the group consisting of BAK at 0.01% to 0.02% weight by volume, EDTA at 0.005% weight by volume, caprylic acid, citric acid, boric acid, sorbic acid and/or salts, derivatives, and analogues thereof.

Many of the listed additives (for example, BAK, EDTA, etc.) may serve more than one purpose: for example, they can serve as both preservatives and corneal permeation enhancing agents (e.g. BAK), or solubilizing, preservative, and corneal permeation enhancing agents (e.g. citrate).

Buffers and pH adjustors include, but are not limited to, acetate buffers, carbonate buffers, citrate buffers, phosphate buffers and borate buffers. It is understood that various acids or bases can be used to adjust the pH of the composition as needed. pH adjusting agents include, but are not limited to, sodium hydroxide and hydrochloric acid. Antioxidants include, but are not limited to, sodium metabisulfite, sodium thiosulfate, acetylcysteine, butylated hydroxyanisole and butylated hydroxytoluene.

To make the topical compositions of the present invention one first creates an oil phase by mixing one or more surfactants, one or more lipid solubilizers and/or propanediol while heating the mixture to greater than 90 C. Next, one adds one or more TKI(s) of the present invention and allows the mixture to cool to room temperature. Next, one creates a water phase by adding a tonicity adjustor, a viscosity enhancer and optionally one or more preservatives and/or buffers. Last, one adds the water phase into oil phase slowly to a final ratio of 3:1 water to oil. To achieve a final concentration of TKI of about 0.25% w/v an initial concentration of 1.0% w/v of the TKI salt is used.

In one embodiment an ophthalmological composition of the present invention comprises:
  cabozantinib mesylate at a concentration wherein the final concentration of cabozantinib is about 0.25% w/v;
  from about 1% to about 15% w/v of a surfactant selected from the group consisting of polyoxyl 40 castor oil (Cremophor® EL; Cremophor is registered trademark of BASF SE Corporation), polyoxyl 40 stearate, Span® 20-80 and a cyclodextrin;
  from about 0.50% to about 1.0% w/v carboxymethyl cellulose (1%=2,500 cps);
  from about 0.1% to about 0.3% w/v glycerin or about 0.037% w/v sodium chloride;
  about 0.02% w/v benzalkonium chloride;
  about 5 millimolar borate or phosphate buffer;
wherein the pH is from about 6.5 to about 8.0.

In another embodiment an ophthalmological composition of the present invention comprises:
  about 0.25% w/v cabozantinib mesylate;
  about 5.5% w/v polyoxyl 35 castor oil or 5.5% w/v polyoxyl 40 stearate;
  about 0.80% w/v carboxymethyl cellulose (1%=2,500 cps);
  about 0.30% w/v glycerin;
  about 0.02% w/v benzalkonium chloride;
  about 5 millimolar borate buffer;
  about 0.015% w/v EDTA;
  from about 1% to about 5% w/v polyethylene glycol, propylene glycol or a combination thereof; and
  optionally, cocamidopropyl betaine at a concentration from about 0.001% to about 0.1% w/v;
wherein the pH is from about 7.0 to about 7.5.

In another embodiment an ophthalmological composition of the present invention comprises:
  cabozantinib mesylate at a concentration wherein the final concentration of cabozantinib is about 0.05% to 0.50% w/v;

about 5.5% w/v polyoxyl 40 castor oil, 5.5% w/v polyoxyl 40 stearate, or Captisol®;
about 0.5% to 10% w/v propanediol
about 0.80% w/v carboxymethyl cellulose (1%=2,500 cps);
about 0.30% w/v glycerin;
about 0.02% w/v benzalkonium chloride;
about 5 millimolar borate buffer;
about 0.015% w/v EDTA;
from about 1% to about 5% w/v polyethylene glycol, propylene glycol or a combination thereof;
optionally, from about 0.005% to about 0.05% w/v cocamidopropyl betaine;
optionally, from about 0.1% to about to 10% w/v squalene; and
optionally, from about 0.01% to about 10% w/v sodium lauryl sulfate or sodium lauryl ether sulfate;
wherein the pH is from about 7.0 to about 7.5.

In another embodiment an ophthalmological composition of the present invention comprises:
cabozantinib mesylate, cabozantinib sulfate, foretinib mesylate or foretinib sulfate at a concentration wherein the final concentration of cabozantinib or foretinib is from about 0.05% to about 0.75% w/v;
about 3.75% w/v propanediol;
about 21.23% w/v dimethyl isosorbide;
from about 5.0% to about 10% w/v Span® 20;
about 0.75% w/v CMC;
about 0.25% w/v NaCl;
about 0.01% w/v BAK;
about 5 mM phosphate buffer; and
from about 67.56% to about 62.56% w/v sterile water.

In another embodiment an ophthalmological composition of the present invention comprises:
cabozantinib mesylate at a concentration wherein the final concentration of cabozantinib is about 0.25% w/v;
about 10% w/v polyoxyl 35 castor oil;
from about 0.70% to about 0.80% w/v carboxymethyl cellulose;
from about 0.1% to about 0.3% w/v glycerin;
about 1 mM to 10 mM borate buffer;
optionally from about 0.005% to about 0.10% w/v sodium lauryl sulfate;
from about 0.005% to about 0.10% w/v cocamidopropyl betaine; and
optionally from about 0.10% to about 10% w/v squalene;

In another embodiment an ophthalmological composition of the present invention comprises:
axitinib sulfate, axitinib mesylate, tivozanib sulfate or tivozanib mesylate at a concentration wherein the final concentration of axitinib or tivozanib is about 0.25% w/v;
INCB280 sulfate, INCB280 mesylate, tivantinib sulfate or tivantinib mesylate at a concentration wherein the final concentration of INCB280 or tivantinib is about 0.25% w/v;
about 3.75% w/v propanediol;
about 21.23% w/v dimethyl isosorbide;
from about 5.0% to about 10% w/v Span® 20;
about 0.75% w/v CMC;
about 0.25% w/v NaCl;
about 0.01% w/v BAK;
about 5 mM phosphate buffer; and
from about 67.56% to about 62.56% w/v sterile water.

The following Examples are provided solely for illustrative purposes and are not meant to limit the invention in any way.

Example 1—Solubilized/Emulsified Cabozantinib Malate (or Mesylate) Salt and Efficacy Final Composition
0.25% w/v cabozantinib;
3.75% w/v propanediol;
21.23% w/v dimethyl isosorbide;
5.0% to 10% w/v Span® 20;
0.75% w/v CMC;
0.25% w/v NaCl;
0.01% w/v BAK;
5 mM phosphate buffer; and
67.56% to 62.56% w/v sterile water.

Process
1. Oil Phase
  a. Propanediol and dimethyl isosorbide were mixed and heated to greater than 90 C.
  b. 1% w/v Cabozantinib malate or mesylate and Span® 20 were added and mixture was cooled to room temperature.
2. Water Phase
  CMC, BAK, NaCl and phosphate buffer were mixed.
3. Water phase was added into oil phase slowly to a final ratio of 3:1 water to oil.
Notes: Cabozantinib malate or mesylate became soluble in oil phase at about 80 C.

Efficacy

The above formulation was applied topically twice-a-day to both eyes of each of two pigmented rabbits. As a control, a vehicle without cabozantinib was applied similarly to two different rabbits. After four days a single dose was applied. On day five tissue levels of the posterior vitreous and plasma levels were assayed. Surprisingly, cabozantinib was measured at 0.99 nanomolar in the posterior vitreous. This is nearly 30 times more than the IC50 for VEGFR2 (0.035 nanomolar) and about equal to the IC50 for c-MET (1.3 nanomolar). Slit lamp and fundus exams were completely normal except for slight conjuctival follicle formation in the treated eyes. This result demonstrates substantial posterior vitreous accumulation of the cabozantinib sufficient to provide anti-VEGFR2 clinical effect and retard intraocular and particularly retinal neovascularization. Such a result also should be sufficient to retard other forms of neovascularization such as in the retina or choroid. A prolonged twice-daily administration, followed by a period of once-daily administration once appropriate levels of cabozantinib are achieved, should ensure the minimum concentration of cabozantinib is achieved to inhibit the c-MET receptor of the human eye.

Additionally, average plasma concentrations were less than 12.5 nanograms per milliliter demonstrating low systemic absorption typical with compositions of the present invention but surprising over the prior art.

Example 2—Solubilized/Suspension Cabozantinib Malate (or Mesylate)

Final Composition
0.02%-0.80% w/v cabozantinib;
1% to 5% w/v propanediol;
1% to 15% w/v sodium lauryl sulfate or sodium lauryl ether sulfate;
1.0% to 10% w/v Span® 20, polyoxyl 40 stearate, polyoxyl 40 castor oil (Cremophor® EL), or Captisol® (negative anionic gamma cyclodextrin) or combination thereof;
0.75% to 1.0% w/v CMC;
0.10% to 0.30% w/v glycerin;

0.02% w/v BAK;
1 mM to 10 mM borate or phosphate buffer;
sterile water; and optionally one or more of the following excipients:
from about 0.005% to about 0.10% w/v cocamidopropyl betaine;
from about 0.10% to about 10% w/v dimethyl isosorbide, squalene or a combination thereof;
from about 1% to about 4% w/v mannitol or other polyol;
about 0.015% w/v citrate or EDTA; and
from about 0.1% to about 10% w/v PEG 400 or other low molecular weight PEG.

Process
1. Oil Phase
   a. Sodium lauryl sulfate (SLS), propanediol (PG), 0.05% to 1.0% w/v cabozantinib malate or mesylate, and optionally dimethyl isosorbide and/or squalene were mixed to create an oil phase mixture, where the ratio of SLS to PG was from about 1:1 to about 10:1; more preferably from about 7:1 to about 9:1;
   b. The oil phase mixture was then swirled over ice or with mild heating up to 80 C as needed to fully solubilize the oil phase mixture;
   c. the solubilized oil phase mixture is then cooled to room temperature. The initial oil phase concentration of SLS may be from about 2% to about 85% w/v; about 70% w/v is preferred.
2. Water Phase
   CMC, BAK, glycerin, citrate or EDTA, surfactant and phosphate buffer were mixed
3. Water phase was mixed into oil phase slowly to a final ratio of 1:1 to 10:1 water to oil with addition of water phase volume in ⅓ to ¼ increments.

Note the final concentration of cabozantinib is from about 0.02% to about 0.8% w/v.

Example 3—Solubilized/Suspension Cabozantinib Malate (or Mesylate)

Final Composition
1% w/v cabozantinib;
10% w/v dimethyl sulfoxide ("DMSO");
1% w/v sodium lauryl sulfate ("SLS");
5.5% w/v polyoxyl 40 stearate,
1.0% w/v carboxymethyl cellulose ("CMC");
0.30% w/v citrate;
0.2% w/v ascorbate
0.02% w/v benzalkonium chloride ("BAK"); and
4 mM borate buffer.
pH 7.0

Process
1. Solubilizing Phase
   a. 100 mg of cabozantinib malate was mixed into 1 mL of dimethyl sulfoxide.
   b. The solubilizing phase mixture was then swirled over ice or while heating up to 80 C as needed to fully solubilize the oil phase mixture;
   c. The solubilizing phase mixture is then cooled to room temperature. The initial solubilizing phase concentration of cabozantinib is 10% w/v.
2. Water Phase
   1.1% w/v SLS, 6.1% w/v polyoxyl 40 stearate, 1.1% w/v CMC, 0.33% w/v citrate, 0.22% w/v ascorbate, 0.022% w/v BAK and 4.4 mM borate buffer were mixed wherein w/v denotes weight by volume of the water phase;
3. Water phase was mixed into solubilizing phase slowly to a final ratio of 9:1 water to solubilizing phase with addition of water phase volume in ⅓ to ¼ increments.

Note the final concentration of cabozantinib is 1.0% w/v.

Example 4—Solubilized Cabozantinib Malate (or Mesylate)

Final Composition
0.37% w/v cabozantinib;
30% w/v dimethyl sulfoxide ("DMSO");
7.0% w/v polyoxyl 40 stearate,
0.80% w/v carboxymethyl cellulose ("CMC");
0.02% w/v benzalkonium chloride ("BAK"); and Process
1. Solubilizing Phase
   a. 18.5 mg of cabozantinib malate/mesylate was mixed into 1.5 mL of DMSO;
   b. The solubilizing phase mixture was then swirled over ice or while heating up to 80 C as needed to fully solubilize the oil phase mixture;
   c. The solubilizing phase mixture was then cooled to room temperature. The initial solubilizing phase concentration of cabozantinib is 1.2% w/v.
2. Water Phase
   10.0% w/v polyoxyl 40 stearate, 1.1% w/v CMC and 0.028% w/v BAK were mixed, wherein w/v denotes weight by volume of the water phase;
3. Water phase was mixed into solubilizing phase dropwise (preferably in ⅓ to ¼ increments) to a final ratio of 2.3:1 water to solubilizing phase.

Example 5—Unit Dose Container

A tyrosine kinase inhibitor of the present invention can be packaged in a convenient dual chamber unit dose pack allowing complete mixing prior to installation. An assembly comprising two chambers of a unit-dose container are separated by an impermeable thin membrane, or thick membrane with thin central region. Lyophilized tyrosine kinase inhibitor is placed within the base of the unit dose container and sealed at its end creating a lyophilized chamber. Preferably the lyophilized chamber is vacuum sealed and/or purged of air with nitrogen gas both before and while being sealed. An ophthalmologically effective diluent formulation is placed at the apex of the unit dose and sealed at its end creating a diluent chamber. The user may then simply pinch the diluent chamber firmly, creating a break in the impermeable membrane between the lyophilized chamber and diluent chamber and releasing the lyophilized tyrosine kinase inhibitor into the diluent chamber with premixing resulting in a suspension or a solubilized solution prior to subject instillation.

The assembly may be optionally designed to effect an automatic compression of the diluent chamber causing the impermeable membrane to rupture and deliver the drug into the diluent chamber. An example of such an automatic compression may occur by placing the unit dose packs in a rack assembly where an upper plastic planar assembly is designed with a smaller opening than the diameter of the unit dose pack at its apex (i.e. the diluent chamber), wherein pulling a tab of the unit dose may then squeeze the upper chamber and effect its internal rupture and mixing of the lyophilized tyrosine kinase inhibitor and ophthalmologically effective diluent.

What is claimed is:
1. A method for treating a disease caused by intraocular neovascularization or leakage selected from the group con- sisting of diabetic macular edema and diabetic proliferative retinopathy, comprising administering to a patient in need thereof an ophthalmological composition comprising an active ingredient consisting of one or more tyrosine kinase inhibitors selected from the group consisting of axitinib, cabozantinib, foretinib, regorafenib, ponatinib, motesanib, cediranib, tivozanib, sorafenib, LY2457546, MGCD-265, MGCD-510, tivantinib, AMG458, JNJ-3887, EMD1214063, BMS794833, PHI1665752, SGX-523 and INCB280 or any pharmaceutically acceptable salts or esters thereof, wherein the route of administration is topical, subconjunctival injection, intravitreal injection or a combination thereof.

2. The method of claim 1 wherein the ophthalmological composition further comprises a surfactant.

3. The method of claim 1 wherein the ophthalmological composition further comprises propanediol at a concentration from about 1% to about 10% weight by total volume of the composition.

4. The method of claim 3 further comprising one or more surfactants or lipid solubilizers each at a concentration from about 1% to about 21% weight by total volume of the composition.

5. The method of claim 4 wherein the one or more surfactants or lipid solubilizers is selected from the group consisting of sodium lauryl ether sulfate, sodium lauryl sulfate, dimethyl isosorbide, sorbitan monolaurate, sorbitan monopalmitate, sorbitan monostearate, sorbitan monooleate, polysorbate 20-80, a cyclodextrin, squalene, a second propylene glycol, a polyethylene glycol, a poloxamer, a polyoxyl and a combination thereof.

6. The method of claim 5 wherein the one or more surfactants or lipid solubilizers is sodium lauryl sulfate at a concentration from about 0.5% to about 10.0% weight by total volume of the composition.

7. The method of claim 6 further comprising a viscosity enhancer selected from the group consisting of carboxymethyl cellulose, carboxypropylmethyl cellulose, hydroxypropyl cellulose, hydroxyethyl cellulose, and hydroxypropylmethyl cellulose and a combination thereof.

8. The method of claim 1 wherein the one or more tyrosine kinase inhibitors is one tyrosine kinase inhibitor selected from the group consisting of cabozantinib, foretinib, MGCD-265 and MGCD-510.

* * * * *